(12) United States Patent
Nair et al.

(10) Patent No.: US 9,108,893 B2
(45) Date of Patent: Aug. 18, 2015

(54) PROCESS FOR PRODUCING CYCLOHEXYLBENZENE

(75) Inventors: Hari Nair, Houston, TX (US); Christopher L. Becker, Manhattan, KS (US); James R. Lattner, LaPorte, TX (US); Jihad M. Dakka, Whitehouse Station, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/348,077

(22) PCT Filed: Sep. 5, 2012

(86) PCT No.: PCT/US2012/053766
§ 371 (c)(1),
(2), (4) Date: Jul. 18, 2014

(87) PCT Pub. No.: WO2013/058882
PCT Pub. Date: Apr. 25, 2013

(65) Prior Publication Data
US 2015/0126782 A1    May 7, 2015

Related U.S. Application Data

(60) Provisional application No. 61/548,080, filed on Oct. 17, 2011.

(51) Int. Cl.
| | |
|---|---|
| *C07C 45/53* | (2006.01) |
| *C07C 37/08* | (2006.01) |
| *C07C 2/74* | (2006.01) |
| *C07C 407/00* | (2006.01) |
| *C07C 5/367* | (2006.01) |
| *C07C 7/09* | (2006.01) |

(52) U.S. Cl.
CPC . *C07C 2/74* (2013.01); *C07C 5/367* (2013.01); *C07C 7/09* (2013.01); *C07C 37/08* (2013.01); *C07C 45/53* (2013.01); *C07C 407/00* (2013.01); *C07C 2101/14* (2013.01); *C07C 2529/08* (2013.01); *C07C 2529/18* (2013.01); *C07C 2529/70* (2013.01); *C07C 2529/74* (2013.01); *C07C 2529/76* (2013.01)

(58) Field of Classification Search
CPC ............ C07C 45/53; C07C 37/08; C07C 2/74
USPC ............................ 568/354, 798; 585/252, 467
See application file for complete search history.

(56) References Cited

U.S. PATENT DOCUMENTS

| | | | |
|---|---|---|---|
| 3,197,399 A | 7/1965 | Wight et al. | |
| 3,201,356 A | 8/1965 | Kress et al. | |
| 3,347,945 A | 10/1967 | Slaugh | |
| 3,390,101 A | 6/1968 | Csicsery | |
| 3,412,165 A | 11/1968 | Slaugh et al. | |
| 3,536,771 A | 10/1970 | Graff | |
| 3,760,017 A | 9/1973 | Arkell et al. | |
| 3,760,018 A | 9/1973 | Suggitt et al. | |
| 3,760,019 A | 9/1973 | Crone, Jr. et al. | |
| 3,784,617 A | 1/1974 | Suggitt et al. | |
| 3,784,618 A | 1/1974 | Suggitt et al. | |
| 3,786,106 A | 1/1974 | Zuech et al. | |
| 3,839,477 A | 10/1974 | Suggitt et al. | |
| 3,864,421 A * | 2/1975 | Suggitt .................. | 585/263 |
| 3,957,687 A | 5/1976 | Arkell et al. | |
| 3,962,362 A | 6/1976 | Suggitt | |
| 4,021,490 A | 5/1977 | Hudson | |
| 4,094,918 A | 6/1978 | Murtha et al. | |
| 4,122,125 A | 10/1978 | Murtha et al. | |
| 4,152,362 A | 5/1979 | Murtha | |
| 4,177,165 A | 12/1979 | Murtha et al. | |
| 4,206,082 A | 6/1980 | Murtha et al. | |
| 4,219,687 A | 8/1980 | Dolhyj et al. | |
| 4,219,689 A | 8/1980 | Murtha | |
| 4,268,699 A | 5/1981 | Murtha et al. | |
| 4,329,531 A | 5/1982 | Murtha et al. | |
| 4,380,683 A | 4/1983 | Dolhyj et al. | |

(Continued)

FOREIGN PATENT DOCUMENTS

| | | |
|---|---|---|
| EP | 0 293 032 | 11/1988 |
| EP | 0 338 734 | 10/1989 |
| EP | 0 387 080 | 9/1990 |
| JP | 2005-342644 | 12/2005 |
| WO | 95/31421 | 11/1995 |
| WO | 97/17290 | 5/1997 |
| WO | 01/53236 | 7/2001 |
| WO | 01/74767 | 10/2001 |
| WO | 2005/118476 | 12/2005 |
| WO | 2009/021604 | 2/2009 |
| WO | 2009/038900 | 3/2009 |
| WO | WO2009/102517 A1 * | 8/2009 |

OTHER PUBLICATIONS

Borodina et al., "Hydroalkylation of Benzene and Ethylbenzene over Metal Containing Zeolite Catalysts", Microporous and Mesoporous Materials, 2007, vol. 105, pp. 181-188.

(Continued)

*Primary Examiner* — Sikarl Witherspoon
(74) *Attorney, Agent, or Firm* — Siwen Chen; Stephen A. Baehl

(57) ABSTRACT

In a process for producing cyclohexylbenzene, hydrogen, and benzene are contacted in a first reaction zone under conditions effective to produce a product effluent containing residual benzene in the vapor phase and cyclohexylbenzene in the liquid phase. The product effluent is separated into a first stream that is rich in residual benzene in the vapor phase as compared to the product effluent and a second stream that is rich in cyclohexylbenzene in the liquid phase as compared to the product effluent. At least a portion of the first stream is cooled to condense at least a portion of the residual benzene in the vapor phase to the liquid phase and produce a condensate stream. At least a portion of the condensate stream is recycled to the first reaction zone.

22 Claims, 4 Drawing Sheets

(56) References Cited

U.S. PATENT DOCUMENTS

| | | | |
|---|---|---|---|
| 4,439,409 | A | 3/1984 | Puppe et al. |
| 4,447,554 | A | 5/1984 | Murtha et al. |
| 4,463,207 | A | 7/1984 | Johnson |
| 4,826,667 | A | 5/1989 | Zones et al. |
| 4,954,325 | A | 9/1990 | Rubin et al. |
| 4,962,250 | A | 10/1990 | Dessau et al. |
| 5,037,538 | A | 8/1991 | Chin et al. |
| 5,053,571 | A | 10/1991 | Makkee |
| 5,108,969 | A | 4/1992 | Del Rossi et al. |
| 5,118,896 | A | 6/1992 | Steigelmann et al. |
| 5,146,024 | A | 9/1992 | Reed |
| 5,236,575 | A | 8/1993 | Bennett et al. |
| 5,250,277 | A | 10/1993 | Kresge et al. |
| 5,292,976 | A | 3/1994 | Dessau et al. |
| 5,334,795 | A | 8/1994 | Chu et al. |
| 5,362,697 | A | 11/1994 | Fung et al. |
| 5,384,296 | A | 1/1995 | Tsao |
| 5,488,194 | A | 1/1996 | Beck et al. |
| 5,554,274 | A | 9/1996 | Degnan et al. |
| 5,557,024 | A | 9/1996 | Cheng et al. |
| 5,705,729 | A | 1/1998 | Huang |
| 6,037,513 | A * | 3/2000 | Chang et al. ............ 585/467 |
| 6,077,498 | A | 6/2000 | Diaz Cabanas et al. |
| 6,133,470 | A | 10/2000 | Beck et al. |
| 6,489,529 | B1 | 12/2002 | Cheng et al. |
| 6,504,070 | B2 | 1/2003 | Matsumoto et al. |
| 6,506,953 | B1 | 1/2003 | Cheng et al. |
| 6,730,625 | B1 | 5/2004 | Chang et al. |
| 6,756,030 | B1 | 6/2004 | Rohde et al. |
| 6,781,025 | B2 | 8/2004 | Dandekar et al. |
| 6,936,744 | B1 | 8/2005 | Cheng et al. |
| 7,488,861 | B2 | 2/2009 | Boyer et al. |
| 7,579,511 | B1 | 8/2009 | Dakka et al. |
| 7,910,778 | B2 | 3/2011 | Chen et al. |
| 2003/0083527 | A1 | 5/2003 | Kuhnle et al. |
| 2004/0092757 | A1 | 5/2004 | Oguchi et al. |
| 2005/0158238 | A1 | 7/2005 | Tatsumi et al. |
| 2008/0027256 | A1 | 1/2008 | Roth et al. |
| 2008/0027259 | A1 | 1/2008 | Roth et al. |
| 2008/0045768 | A1 | 2/2008 | Roth et al. |
| 2010/0317895 | A1 | 12/2010 | Buchanan et al. |
| 2011/0037022 | A1 * | 2/2011 | Dakka et al. ............ 252/182.31 |
| 2012/0157718 | A1 | 6/2012 | Bencini et al. |

OTHER PUBLICATIONS

Fan et al., *"Synthesis and Catalytic Properties of a New Titanosilicate Molecular Sieve with the Structure Analogous to MWW-type Lamellar Precursor"*, Journal of Catalyst, 2006, vol. 243, pp. 183-191.

Kim et al., *"Structural Evolution of B-MCM-36 and B-ITQ-2 from B-MCM-22"*, Bull. Korean Chem. Society, 2006, vol. 27, No. 10, pp. 1693-1696.

Lawton et al., *"Zeolite MCM-49: A Three-Dimensional MCM-22 Analogue Synthesized by in Situ Crystallization"*, Journal of Physical Chemistry, 1996, vol. 100, pp. 3788-3798.

Maheshwari et al., *"Layer Structure Preservation During Swelling, Pillaring, and Exfoliation of a Zeolite Precursor"*, Journal of American Chemical Soc., 2008, vol. 130, pp. 1507-1516.

Ruan et al., *"Structure Elucidation of the Highly Active Titanosilicate Catalyst Ti-YNU-1"*, Angew. Chem. Int. Ed., 2005, vol. 44, pp. 6719-6723.

Slaugh et al., *"Hydrodimerization of Benzene to Phenylcyclohexane over Supported Transition Metal Catalysts"*, Journal of Catalysis, 1969, vol. 13, pp. 385-396.

Wu et al., *"Methodology for Synthesizing Crystalline Metallosilicates with Expanded Pore Windows Through Molecular Alkoxysilylation of Zeolitic Lamellar Precursors"*, Journal of American Chemical Soc., 2008, vol. 130, pp. 8178-8187.

Zhicheng et al., *"Static Synthesis of High-Quality MCM-22 Zeolite with High $SiO_2/Al_2O_3$ Ratio"*, Chinese Science Bulletin, 2004, vol. 49, No. 6, pp. 556-561.

* cited by examiner

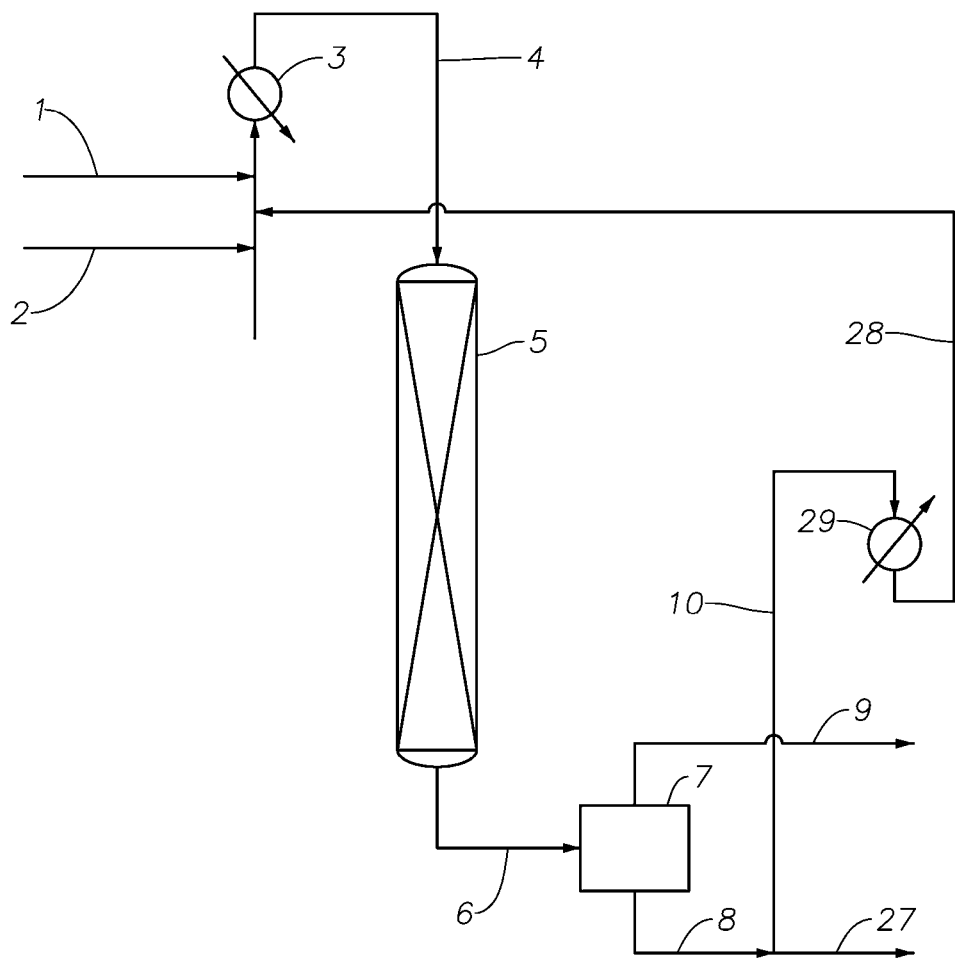
Fig. 1 (Conventional)

PROCESS FOR PRODUCING CYCLOHEXYLBENZENE

PRIORITY CLAIM TO RELATED APPLICATIONS

This application is a National Stage Application of International Application No. PCT/US2012/053766 filed Sep. 5, 2012, which claims priority to U.S. Provisional Application Ser. No. 61/548,080 filed Oct. 17, 2011, the disclosures of which are fully incorporated herein by their reference.

FIELD

The present invention relates to a process for producing cyclohexylbenzene and for converting the resultant cyclohexylbenzene into phenol and cyclohexanone.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide, and then cleavage of the hydroperoxide to produce equimolar amounts of phenol and acetone. However, the world demand for phenol is growing more rapidly than that for acetone. In addition, due to a developing shortage, the cost of propylene is likely to increase.

Thus, a process that uses higher alkenes instead of propylene as feed and coproduces higher ketones, such as cyclohexanone, rather than acetone may be an attractive alternative route to the production of phenols. For example, there is a growing market for cyclohexanone, which is used as an industrial solvent, as an activator in oxidation reactions, and in the production of adipic acid, cyclohexanone resins, cyclohexanone oxime, caprolactam, and nylon 6.

It is known from, for example, U.S. Pat. No. 6,037,513 that cyclohexylbenzene can be produced by contacting benzene with hydrogen in the presence of a bifunctional catalyst comprising a molecular sieve of the MCM-22 family and at least one hydrogenation metal selected from palladium, ruthenium, nickel, cobalt, and mixtures thereof. The contacting is conducted at a temperature of about 50° C. to 350° C., a pressure of about 100 kPa to 7000 kPa, a benzene to hydrogen molar ratio of about 0.01 to 100, and a WHSV of about 0.01 to 100. In addition to cyclohexylbenzene, the product of the hydroalkylation reaction comprises cyclohexane, dicyclohexylbenzene, bicyclohexane, and a significant amount of benzene. The '513 patent also discloses that the resultant cyclohexylbenzene can be oxidized to the corresponding hydroperoxide which is then decomposed to the desired phenol and cyclohexanone co-product.

One problem with producing cyclohexylbenzene by the hydroalkylation of benzene over an acid catalyst, such as MCM-22, is that the reaction is highly exothermic and so it is normally necessary to provide for cooling of the reagents. This is conveniently achieved by recycling at least part of the liquid phase reaction product although, since the product contains high concentrations of cyclohexylbenzene, this has the unintended result of increasing the concentration of unwanted dicyclohexylbenzene and bicyclohexane in the product and hence decreasing the yield of the desired cyclohexylbenzene. There is, therefore, interest in finding alternative processes for cooling the reagents in the hydroalkylation process.

One such process is disclosed in U.S. Published Patent Application No. 2010/0317895, in which (a) hydrogen and a liquid feed comprising benzene are introduced into a reaction zone, where the benzene reacts with the hydrogen to produce cyclohexylbenzene; (b) a liquid effluent stream comprising cyclohexylbenzene and benzene is removed from said reaction zone; (c) the liquid effluent stream is divided into at least first and second portions, wherein the ratio of the mass of the effluent stream first portion to the mass of effluent stream second portion is at least 2:1; (d) the effluent stream first portion is cooled; and (e) the cooled effluent stream first portion is recycled to the reaction zone.

According to the invention, an alternative process for cooling the reagents in the benzene hydroalkylation process is provided, in which the hydroalkylation conditions are adjusted to produce a significant amount of vaporization of the benzene in the reactor. This vaporization not only provides direct cooling but also, since cyclohexylbenzene is much less volatile than benzene and cyclohexane, the vapor phase at the reactor exit contains very little cyclohexylbenzene. Thus, by cooling and condensing the vapor phase effluent and then recycling the condensed stream back to the reactor, additional reactor cooling is achieved while restricting the amount of cyclohexylbenzene fed back to reactor and hence minimizing the production of unwanted dicyclohexylbenzene and bicyclohexane.

SUMMARY

In one aspect, the invention relates to a process for producing cyclohexylbenzene comprising:

(a) contacting hydrogen and benzene in a first reaction zone under conditions effective to produce a product effluent comprising cyclohexylbenzene and residual benzene, wherein at least a portion of the residual benzene is in the vapor phase and at least a portion of the cyclohexylbenzene is in the liquid phase;

(b) separating the product effluent into (i) a first stream that is rich in residual benzene in the vapor phase as compared to the product effluent; and (ii) a second stream that is rich in cyclohexylbenzene in the liquid phase as compared to the product effluent;

(c) cooling at least a portion of the first stream to condense at least a portion of the residual benzene in the vapor phase to the liquid phase and produce a condensate stream; and (d) recycling at least a portion of the condensate stream to the first reaction zone.

Conveniently, the first stream further comprises cyclohexane and, after removal of the condensate stream in the cooling step (c), at least a portion of the remaining first stream is contacted with a dehydrogenation catalyst under dehydrogenation conditions effective to convert cyclohexane to benzene.

In one embodiment, the condensate stream contains less than 0.5 wt % of cyclohexylbenzene, based upon the total weight of the condensate stream.

In a further aspect, the invention relates to a process for producing cyclohexylbenzene comprising:

(a) contacting hydrogen and benzene in a first reaction zone under conditions effective to produce a first product effluent comprising cyclohexylbenzene and residual benzene, wherein at least a portion of the residual benzene is in the vapor phase;

(b) separating the first product effluent into (i) a first stream that is rich in residual benzene in the vapor phase as compared to the first product effluent; and (ii) a second stream that comprises residual benzene and is rich in cyclohexylbenzene in the liquid phase as compared to the first product effluent;

(c) contacting the second stream with hydrogen in a second reaction zone under conditions effective to convert at least a portion of the residual benzene to cyclohexylbenzene and produce a second product effluent comprising cyclohexylbenzene and further residual benzene, wherein at least a portion of the further residual benzene is in the vapor phase;

(d) separating the second product effluent into a third stream that is rich in further residual benzene in the vapor phase as compared to the second product effluent, and a fourth stream that is rich in cyclohexylbenzene in the liquid phase as compared to the second product effluent;

(e) cooling at least a portion of the first stream and the third stream to condense at least a portion of the residual benzene and further residual benzene and produce a condensate stream; and (f) recycling at least a portion of the condensate stream to at least one of the first reaction zone and the second reaction zone.

In yet a further aspect, the invention relates to a process for producing phenol comprising:

(a) contacting benzene and hydrogen in a first reaction zone under conditions effective to produce a product effluent comprising cyclohexylbenzene and residual benzene, wherein at least a portion of the residual benzene is in the vapor phase;

(b) separating the product effluent into (i) a first stream that is rich in residual benzene in the vapor phase as compared to the product effluent; and (ii) a second stream that is rich in cyclohexylbenzene in the liquid phase as compared to the product effluent;

(c) cooling at least a portion of the first stream to condense at least a portion of the residual benzene and produce a condensate stream that is rich in residual benzene;

(d) recycling at least a portion of the condensate stream to the first reaction zone;

(e) oxidizing at least a portion of the second stream under conditions sufficient to form at least some cyclohexylbenzene hydroperoxide; and (f) cleaving at least a portion of the cyclohexylbenzene hydroperoxide to form phenol and cyclohexanone.

BRIEF DESCRIPTION OF THE DRAWINGS

FIG. 1 is a schematic diagram of a conventional process for producing cyclohexylbenzene according to a first example of the invention.

DETAILED DESCRIPTION OF THE EMBODIMENTS

Figure 2:
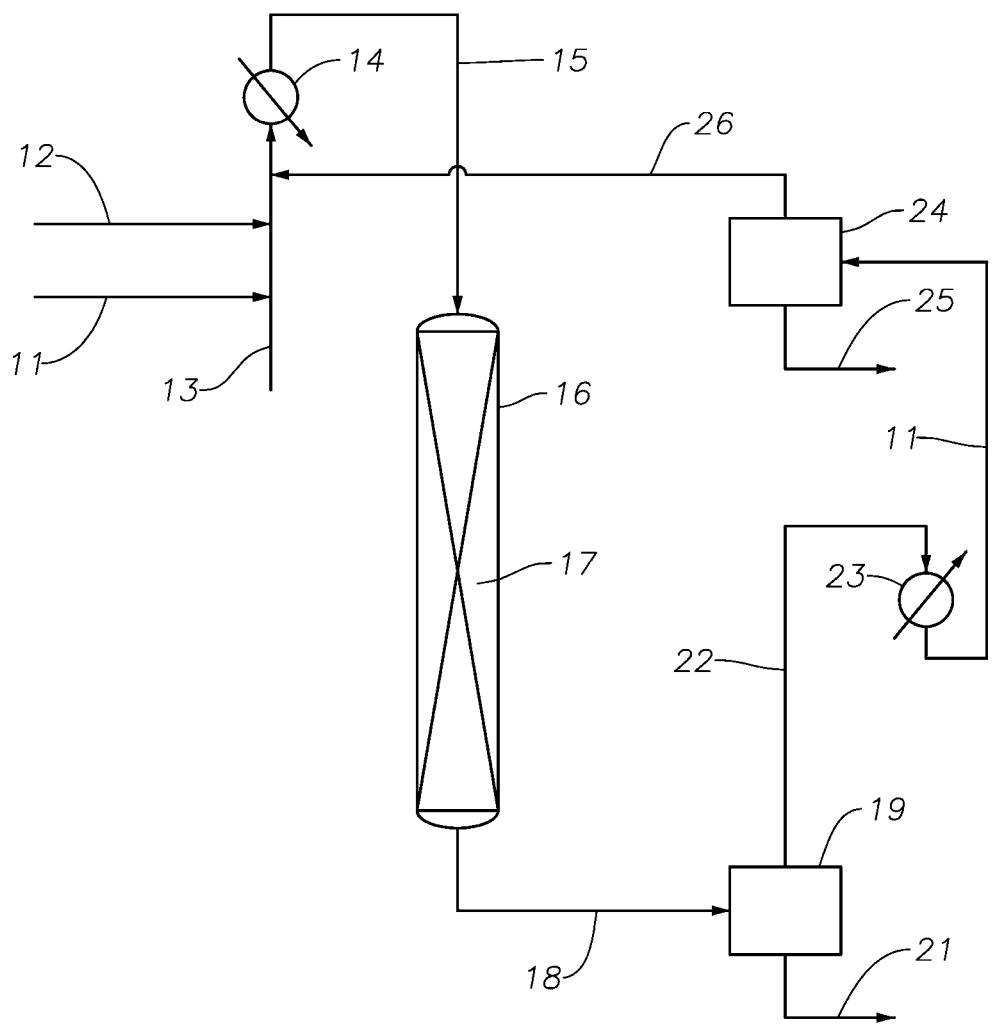
FIG. 2 is a schematic diagram of a process for producing cyclohexylbenzene according to a first example of the invention.

Described herein is a process of producing cyclohexylbenzene by the hydroalkylation of benzene and more particularly to an integrated process for producing phenol and cyclohexanone in which benzene is first hydroalkylated to produce cyclohexylbenzene, then the cyclohexylbenzene is oxidized to cyclohexylbenzene hydroperoxide and the cyclohexylbenzene hydroperoxide is subsequently cleaved to the desired phenol and cyclohexanone.

In the present process, the hydroalkylation is conducted under conditions such that the product effluent is a mixed phase stream containing cyclohexylbenzene and benzene in which the cyclohexylbenzene is largely in the liquid phase but at least a portion of the benzene is in the vapor phase. The product effluent is then separated, for example, in a flash drum, into a vapor phase stream containing benzene, and a liquid phase stream containing cyclohexylbenzene. The liquid phase stream is removed for recovery of the cyclohexylbenzene product, while the vapor phase stream is cooled to condense at least a portion of the benzene from the vapor phase stream and produce a benzene-rich condensate stream. The condensate stream is then recycled back to the hydroalkylation reactor. This condensed liquid recycle, along with the cooling effect due to the partial vaporization of the benzene in the reactor, helps to control the reaction exotherm while restricting the amount of cyclohexylbenzene fed back to the reactor to extremely small amounts, thereby minimizing unwanted conversion of cyclohexylbenzene to dicyclohexylbenzene.

Production of Cyclohexylbenzene

In the present process, cyclohexylbenzene is produced by hydroalkylation of benzene, which involves the partial hydrogenation of one benzene molecule to cyclohexene, followed by the alkylation of another benzene molecule with the cyclohexene. With the proper bifunctional catalyst, the first step occurs on the metal function and the second step on the acid function. The reactions may be summarized as follows:

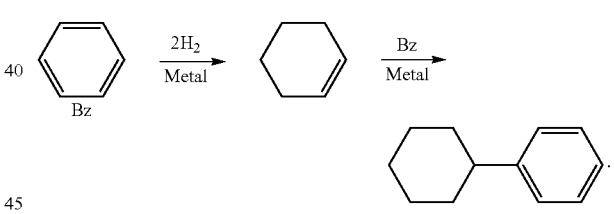

The alkylation reaction is fast, relative to hydrogenation, so the intermediate cyclohexene concentration is minimal. However, some of the benzene hydrogenates completely to cyclohexane:

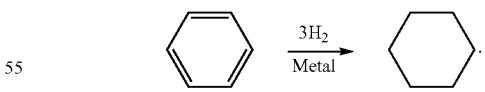

In addition, some of the intermediate cyclohexene will alkylate a cyclohexylbenzene (CHB) molecule, rather than a benzene molecule, to form dicyclohexylbenzene:

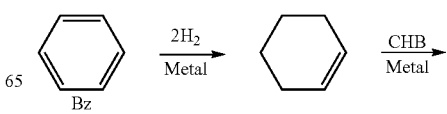

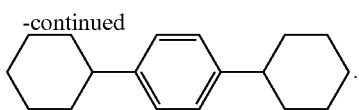

The proportion of cyclohexene that alkylates benzene versus cyclohexylbenzene is roughly proportional to the concentrations of benzene versus cyclohexylbenzene in the liquid phase surrounding the catalyst. Thus, as will be described in detail below, the present process seeks to minimize the concentration of cyclohexylbenzene in the liquid phase in the hydroalkylation reactor.

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values, but typically is arranged such that the molar ratio of hydrogen to benzene in the hydroalkylation feed is between about 0.01:1 to about 20:1, for example between about 0.15:1 and about 15:1, such as between about 0.4:1 and about 4:1, for example between about 0.4:1 and about 0.9:1. In various embodiments, the hydroalkylation reaction is conducted in the presence of a stoichiometric excess of hydrogen.

In addition to the benzene and hydrogen, a diluent, which is substantially inert under hydroalkylation conditions, may be supplied to the hydroalkylation reaction. Typically the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, generally the diluent is added in an amount such that the weight ratio of the diluent to the aromatic compound is at least 1:100; for example at least 1:10, but no more than 10:1, typically no more than 4:1.

The catalyst employed in the hydroalkylation reaction is a bifunctional catalyst comprising a molecular sieve and a hydrogenation metal. The molecular sieve is generally selected from at least one of zeolite beta, mordenite, zeolite X, zeolite Y, and a molecular sieve of the MCM-22 family. Preferably, the molecular sieve comprises an MCM-22 family material. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference;)

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07, and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49; (b) MCM-56; and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 wt % and about 10 wt %, such as between about 0.1 wt % and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from, but composited with, the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is used as in Richard J. Lewis Sr., HAWLEY'S CONDENSED CHEMICAL DICTIONARY (14th ed., John Wiley & Sons, Inc. 2001).

The hydrogenation metal is deposited on the inorganic oxide, conveniently by impregnation, before the metal-containing inorganic oxide is composited with said molecular sieve. Typically, the catalyst composite is produced by co-pelletization, in which a mixture of the molecular sieve and the metal-containing inorganic oxide are formed into pellets at high pressure (generally about 350 kPa to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials, such as clay, silica, and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment, or chemical modification. Suitable metal oxide binders include silica, alumina, zirconia, titania, silica-alumina, silica-magnesia, silica-zirconia, silica-thoria, silica-beryllia, silica-titania, as well as ternary compositions, such as silica-alumina-thoria, silica-alumina-zirconia, silica-alumina-magnesia, and silica-magnesia-zirconia.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones (e.g., in 1-10 reaction zones, or 2-7 reaction zones, or 2-5 reaction zones, or 3 reaction zones), in which at least the hydrogen is introduced to the reaction in stages. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa.

In the present process, the molar ratio of hydrogen to benzene in the feed to the hydroalkylation reactor are controlled so that, although the hydroalkylation reaction occurs in the liquid phase, at least part of the benzene in the reactor is in the vapor phase. As a result, the product effluent leaving the reactor is a mixed phase composition, in which most of cyclohexylbenzene product is in the liquid phase and at least 5 wt %, such as at least 10 wt %, for example at least 25 wt %, even at least 50 wt %, of the benzene is in the vapor phase based upon the total weight of the product effluent. Any cyclohexane by-product will be mainly in the vapor phase, while any dicyclohexylbenzene will be mainly in the liquid phase.

After leaving the reactor, the product effluent is fed to a separator, such as a flash drum, to separate the effluent into (i) a first stream that is rich in benzene the vapor phase (also referred to as "residual benzene," which means benzene remaining in the product effluent from the feed stream after the hydroalkylation reaction occurs) as compared to the product effluent (i.e., the first stream contains a higher wt % of benzene in the vapor phase based upon total weight of the first stream compared to the wt % of benzene in the vapor phase in the product effluent based upon the weight of the product effluent); and (ii) a second stream that is rich in cyclohexylbenzene in the liquid phase as compared to the product effluent (i.e., the second stream contains a higher wt % of cyclohexylbenzene in the liquid phase based upon total weight of the second stream compared to the wt % of cyclohexylbenzene in the liquid phase in the product effluent based upon the weight of the product effluent).

In various embodiments, the first stream contains greater than 50 wt % of residual benzene in the vapor phase, or greater than 70 wt %, or greater than 90 wt %, or greater than 95 wt %, or greater than 99 wt % of benzene in the vapor phase, the wt % based upon the total weight of the first stream. In various embodiments, the second stream contains greater than 50 wt % of cyclohexylbenzene in the liquid phase, or greater than 70 wt %, or greater than 90 wt %, or greater than 95 wt %, or greater than 99 wt % of cyclohexylbenzene in the liquid phase, based upon the total weight of the second stream.

In various embodiments, the first stream contains hydrogen, benzene, and cyclohexane together with small quantities of other reaction products such as cyclohexylbenzene, dicyclohexylbenzene, and bicyclohexane. The first stream may contain, for example, less than 5 wt % of other reaction products alone or in combination, or less than 1 wt %, or less than 0.1 wt %, or less than 0.01 wt % of other reaction products alone or in combination based upon the total weight of the first stream. The second stream may contain cyclohexylbenzene and benzene, together with most of the heavier by-products, such as dicyclohexylbenzene and bicyclohexane, together with small quantities of hydrogen and cyclohexane.

The first stream produced in the separator is then cooled to condense at least a portion of the benzene from the first stream and thereby produce a condensate stream that is rich in benzene relative to the first stream (i.e., the condensate stream contains a higher wt % of benzene based upon total weight of the condensate stream compared to the wt % of benzene in the first stream based upon the weight of the first stream) and contains less than 10 wt %, such as less than 5 wt %, for example less than 0.5 wt % of cyclohexylbenzene. Conveniently, the first stream is cooled by at least 10° C., such as to a temperature of 150° C. or less, for example, to a temperature of 130° C. or less. The condensate stream is then recycled back to the hydroalkylation reactor in an amount depending on the operating conditions but generally between about 0.1 to about 50 times the feed rate of fresh make-up benzene to the reactor. The remainder of the first stream left after removal of the benzene-rich condensate is composed mainly of hydrogen and can be recycled back to the hydroalkylation reactor, with or without purification, or used as a hydrogen feed for a different process.

The second stream produced in the separator is composed mainly of cyclohexylbenzene and benzene (i.e., >50 wt % combined by weight of the second stream) and is normally fed to a separation system comprising one or more distillation units for recovery of the cyclohexylbenzene product. In addition, depending on the amount of benzene in the second stream, at least a portion of the second stream (normally after recovery of the cyclohexylbenzene product) can be fed to a second hydroalkylation reaction zone where the benzene is contacted with hydrogen under hydroalkylation conditions to produce a further product effluent comprising cyclohexylbenzene and benzene (also referred to as "further residual benzene," which means benzene remaining in the further product effluent from the second stream after a second hydroalkylation reaction occurs), wherein at least a portion of the benzene is in the vapor phase. This further product effluent may be then separated into a third stream containing benzene primarily in the vapor phase, and a fourth stream containing cyclohexylbenzene primarily in the vapor phase. At least a portion of the third stream is then cooled to condense out a further condensate stream rich in benzene and at least a portion of the further condensate stream is recycled to the first and/or second reaction zone.

In various embodiments, the product effluent contains dicyclohexylbenzene, and the second stream is rich in dicyclohexylbenzene relative to the product effluent (i.e., the second stream contains a higher wt % of dicyclohexylbenzene based upon total weight of the second stream compared to the wt % of dicyclohexylbenzene in the condensate stream based upon the weight of the condensate stream).

Although the present process seeks to maximize the amount of cyclohexylbenzene and minimize the amount of dicyclohexylbenzene, the effluent from the hydroalkylation reaction will inevitably contain some dicyclohexylbenzene by-product. Depending on the amount of this dicyclohexylbenzene, it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, and mordenite. The transalkylation reaction is typically conducted under at least partial liquid phase conditions, which suitably include a temperature of about 100° C. to about 300° C., a pressure of about 800 kPa to about 3500 kPa, a weight hourly space velocity of about 1 $hr^{-1}$ to about 10 $hr^{-1}$ on total feed, and a benzene/dicyclohexylbenzene weight ratio about of 1:1 to about 5:1.

Dealkylation or cracking is also typically effected in a reactor separate from the hydroalkylation reactor, such as a reactive distillation unit, at a temperature of about 150° C. to about 500° C. and a pressure of 15 psig to 500 psig (200 kPa to 3550 kPa) over an acid catalyst, such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia, and mixtures thereof. Generally, the acid catalyst includes at least one aluminosilicate, aluminophosphate, or silicoaluminphosphate of the FAU, AEL, AFI, and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is typically from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

As stated above, another significant by-product of the hydroalkylation reaction is cyclohexane which, in the present process, will mainly be present in the benzene-rich condensate stream. Owing to the similarity in the boiling points of benzene and cyclohexane, it is difficult to remove the cyclohexane from the condensate stream by simple distillation. Depending on the amount of the cyclohexane in the condensate stream, it may be desirable to recycle the cyclohexane with the benzene in the condensate stream to the hydroalkylation reactor to provide some or all of the diluent mentioned above.

In some cases, it may be desirable to supply at least some of the condensate stream to a dehydrogenation reaction zone, where the condensate stream is contacted with a dehydrogenation catalyst under dehydrogenation conditions sufficient to convert at least part of the cyclohexane in the condensate stream to benzene, which again can be recycled to the hydroalkylation reaction. The dehydrogenation catalyst generally comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium, and compounds and mixtures thereof. Typically, the hydrogenation-dehydrogenation component is present in an amount between about 0.1 wt % and about 10 wt % of the catalyst. A suitable inorganic promoter (c) comprises at least one metal or compound thereof selected from Group 1 of the Periodic Table of Elements, such as a potassium compound. Typically, the promoter is present in an amount between about 0.1 wt % and about 5 wt % of the catalyst. Suitable dehydrogenation conditions include a temperature of about 250° C. to about 550° C., a pressure of about atmospheric to about 500 psig (100 kPa to 3550 kPa), a weight hourly space velocity of about 0.2 $hr^{-1}$ to 50 $hr^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{12}$ stream. Similarly, bicyclohexyl (BCH) can lead to separation problems downstream. Thus, at least part of the hydroalkylation reaction product may be treated with a catalyst under conditions to remove at least 1,1-methylcyclopentylbenzene and/or bicyclohexyl from the product. The catalyst is generally an acid catalyst, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

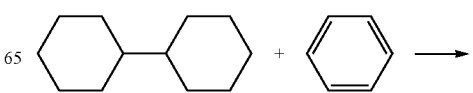

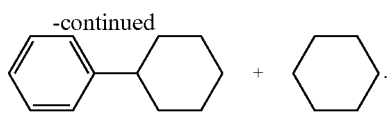

The catalytic treatment can be conducted on the direct product of the hydroalkylation reaction or after distillation of the hydroalkylation reaction product to separate the $C_6$ and/or the heavies fraction.

The cyclohexylbenzene product from the hydroalkylation reaction and any downstream reaction to remove the impurities discussed above is separated from the reaction effluent(s) and is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by contacting the cyclohexylbenzene with an oxygen-containing gas, such as air and various derivatives of air. For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air, or other conventional means.

The oxidation is conducted in the presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, or N-hydroxy-o-benzenedisulphonimide may be used. Preferably, the catalyst is N-hydroxyphthalimide. Another suitable catalyst is N,N',N"-thihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N', N"-trihydroxyisocyanuric acid is employed in an amount between 0.0001 wt % to 15 wt %, such as between 0.001 wt % to 5 wt %, of the cyclohexylbenzene.

Suitable conditions for the oxidation step include a temperature between about 70° C. and about 200° C., such as about 90° C. to about 130° C., and a pressure of about 50 kPa to about 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Typically, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation reaction effluent. Generally, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may further comprise imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

At least a portion of the oxidation reaction effluent may be subjected to a cleavage reaction, with or without undergoing any prior separation or treatment. For example, all or a fraction of the oxidation reaction effluent may be subjected to high vacuum distillation to generate a product enriched in unreacted cyclohexylbenzene and leave a residue which is concentrated in the desired cyclohexyl-1-phenyl-1-hydroperoxide and which is subjected to the cleavage reaction. In general, however, such concentration of the cyclohexyl-1-phenyl-1-hydroperoxide is neither necessary nor preferred. Additionally or alternatively, all or a fraction of the oxidation effluent, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation effluent may be subjected to water washing and then passage through an adsorbent, such as a 3 A molecular sieve, to separate water and other adsorbable compounds, and provide an oxidation composition with reduced water or imide content that may be subjected to the cleavage reaction. Similarly, all or a fraction of the oxidation effluent may undergo a chemically or physically based adsorption, such as passage over a bed of sodium carbonate to remove the imide oxidation catalyst (e.g., NHPI) or other adsorbable components, and provide an oxidation composition reduced in oxidation catalyst or other adsorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Publication No. WO 2009/025939.

Hydroperoxide Cleavage

The final reactive step in the conversion of the cyclohexylbenzene into phenol and cyclohexanone involves the acid-catalyzed cleavage of the cyclohexyl-1-phenyl-1-hydroperoxide produced in the oxidation step.

Generally, the acid catalyst used in the cleavage reaction is at least partially soluble in the cleavage reaction mixture, is stable at a temperature of at least 185° C., and has a lower volatility (higher normal boiling point) than cyclohexylbenzene. Typically, the acid catalyst is also at least partially soluble in the cleavage reaction product. Suitable acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

In various embodiments, the cleavage reaction mixture contains at least 50 weight-parts-per-million (wppm) to 5000 wppm of the acid catalyst, or at least 100 wppm to 3000 wppm, or at least 150 wppm to 2000 wppm of the acid catalyst, or at least 300 wppm to 1500 wppm of the acid catalyst, based upon total weight of the cleavage reaction mixture.

In other embodiments, a heterogeneous acid catalyst is employed for the cleavage reaction, such as molecular sieve, and in particular a molecular sieve having a pore size in excess of 7 Å. . Examples of suitable molecular sieves include zeolite beta, zeolite Y, zeolite X, ZSM-12, and mordenite. In one embodiment, the molecular sieve comprises a FAU type zeolite having a unit cell size less than 24.35 Å, such as less than or equal to 24.30 Å, even less than or equal to 24.25 Å. The zeolite can be used in unbound form or can be combined with a binder, such as silica or alumina, such that the overall catalyst (zeolite plus binder) comprises from about 20 wt % to about 80 wt % of the zeolite.

The cleavage reaction mixture may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is phenol and/or cyclohexanone recycled from the cleavage product after cooling. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

In various embodiments, the cleavage reaction mixture includes cyclohexylbenzene in an amount of at least 50 wt %, or at least 60 wt %, or at least 65 wt %, or at least 70 wt %, or at least 80 wt %, or at least 90 wt %, based upon total weight of the cleavage reaction mixture.

Generally, the cleavage reaction is conducted under conditions including a temperature of about 20° C. to about 200° C., such as about 40° C. to about 120° C. and a pressure of about 100 kPa to about 2000 kPa, such as about 100 kPa to about 1000 kPa, such that the cleavage reaction mixture is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

The major products of the cleavage reaction of cyclohexyl-1-phenyl-1-hydroperoxide are phenol and cyclohexanone, which are present in substantially equimolar proportions and can be recovered from the cleavage effluent by any known method.

The invention will now be more particularly described with reference to the accompanying drawings and the following Examples.

Referring to FIG. 1, a conventional hydroalkylation reactor system is shown. Stream 1 contains hydrogen and stream 2 contains benzene. The ratio of molar flow rates of hydrogen in stream 1 and benzene in stream 2 can vary from 0.1 to 100. Stream 28 contains benzene and reaction products such as cyclohexane, cyclohexylbenzene, dicyclohexylbenzene and bicyclohexane. Streams 1, 2 and 28 are supplied to reactor 5 and can be heated to the desired reaction temperature individually or after combining using heater 3.

The hydroalkylation reactor 5 may be a packed bed reactor loaded with a suitable catalyst and operates at temperatures of about 50° C. to 350° C. and pressures of about 100 kPa to 7000 kPa. The catalyst employed in the hydroalkylation reaction is a bifunctional catalyst comprising a molecular sieve with an acid function and a hydrogenation metal. Suitable molecular sieves include zeolite beta, zeolite X, zeolite Y, and molecular sieves of the MCM-22 family.

As disclosed in U.S. Patent Pub. No. 2011/0037022, when benzene and hydrogen are contacted with the above-mentioned catalysts under hydroalkylation conditions, an effluent stream 6 in liquid phase (containing benzene, cyclohexylbenzene, cyclohexane, dicyclohexylbenzene, bicyclohexane) is obtained, with small quantities of dissolved hydrogen. Under conditions in which the hydrogen is not completely consumed, the effluent stream 6 also has a vapor phase component comprising mainly of hydrogen, benzene, cyclohexane and small amounts of less volatile cyclohexylbenzene, dicyclohexylbenzene and bicyclohexane. The temperature of stream 6 is typically 1-100° C. higher than the feed temperature. It can be desirable to minimize this temperature rise, so that the reaction occurs under conditions approaching isothermal.

The vapor phase can be separated from the liquid phase by means of a flash vessel 7 which operates at the temperature and pressure of stream 6, resulting in a liquid stream 8 and a vapor stream 9. Stream 8 contains benzene, cyclohexylbenzene, cyclohexane, dicyclohexylbenzene and bicyclohexane and is the product stream from the process. Stream 9 contains mainly hydrogen, benzene, cyclohexane and small amounts of less volatile cyclohexylbenzene, dicyclohexylbenzene and bicyclohexane and is at the temperature of the flash vessel 7.

In the conventional scheme, stream 8 would be split into stream 10, which is the product from the process and stream 27 which is to be recycled to the reactor. Streams 10 and 27 have the same composition as stream 8. Stream 27 can further be cooled to lower temperatures using heat exchanger 12. The resultant stream 28 is recycled to the reactor 5.

Example 1

A conventional embodiment according to FIG. 1 was simulated with a hydrogen to benzene feed molar ratio of 1:1.5. The results are provided in Table 1.

Referring to an embodiment of the invention illustrated in FIG. 2, hydrogen (e.g., fresh hydrogen) and benzene (e.g., fresh benzene) are supplied by lines 11 and 12 and are combined in line 13 before being fed to a heater 14 where the temperature of the reagents is increased to the desired reaction temperature. The heated feed is then fed by line 15 to a reactor 16 which contains hydroalkylation catalyst 17 and which is operated under conditions to vaporize part of the benzene feed and produce a mixed phase product effluent in which most of cyclohexylbenzene is in the liquid phase and a portion of the benzene is in the vapor phase. The effluent leaves the reactor 16 through line 18 and is fed to a flash drum 19, which separates the effluent into a liquid stream and a vapor stream.

The liquid stream is removed from the flash drum 19 by line 21 for recovery of the cyclohexylbenzene product, while the vapor stream is removed by line 22 and fed by way of a heat exchanger 23 to a further flash drum 24. The heat exchanger 23 is arranged to cool the vapor steam so that benzene condenses out of the vapor stream and further flash drum 24 separates the cooled vapor stream into a benzene-rich condensate stream and a further vapor stream. The benzene-rich condensate stream is removed from the further flash drum 24 in line 25 and recycled to the reactor 16, without passage through the heater 14, as a low temperature liquid stream. The further vapor stream, which is composed mainly of hydrogen, is removed from the further flash drum 24 in line 26 for mixing with the hydrogen and benzene before the latter are fed to the heater 14.

Example 2

The invention according to FIG. 2 was simulated with a hydrogen to benzene feed molar ratio of 1:1. The results are provided in Table 2.

Example 3

The invention according to FIG. 2 was simulated with a hydrogen to benzene feed molar ratio of 1:1.5. The results are provided in Table 3.

Figure 3:
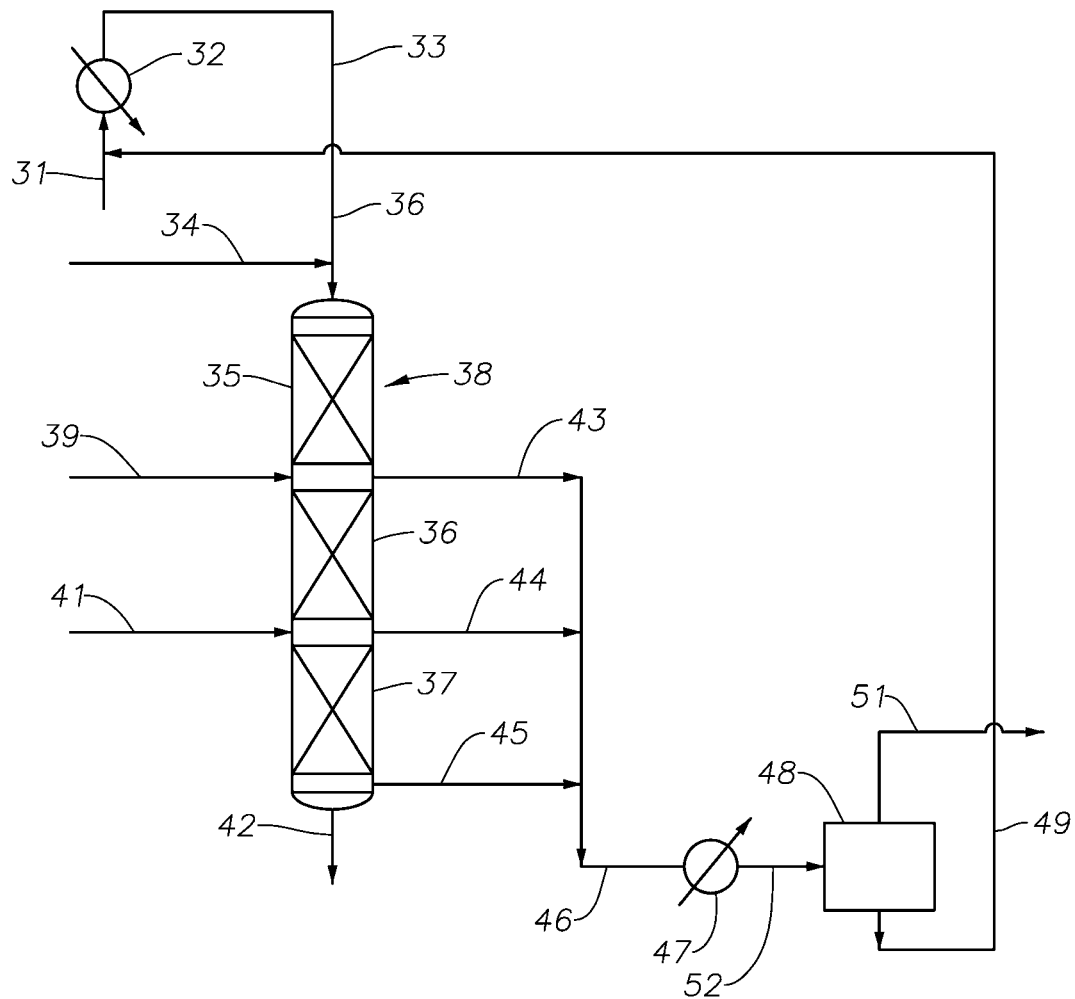
FIG. 3 is a schematic diagram of a process for producing cyclohexylbenzene according to a second example of the invention.

Referring to an embodiment of the invention illustrated in FIG. 3, in a second example, the benzene hydroalkylation is conducted in a plurality of reaction zones with the hydrogen being distributed between the zones. Benzene (e.g., fresh benzene) is introduced to the process by line 31 and is heated to the desired reaction temperature by heater 32. The heated benzene is then fed by line 33, together with a first hydrogen stream (e.g., heated hydrogen) in line 34, to the first of three catalyst-containing reaction zones 35, 36 and 37 connected in series in a reactor 38. It will be understood that the reaction zones may be arranged as illustrated in FIG. 3, or may be separate reactors. The first reaction zone 35 is maintained under conditions to vaporize part of the benzene feed and to convert a portion of the benzene feed to a first mixed phase product in which most of cyclohexylbenzene is in the liquid phase and part of the benzene is in the vapor phase.

The first liquid phase (primarily cyclohexylbenzene) product flows out of the first reaction zone 35 and is mixed with a second hydrogen stream (e.g., heated hydrogen) in line 39 before flowing into the second reaction zone 36. If necessary, the temperature of the second hydrogen stream can be adjusted to effect cooling of the first liquid phase product. Again the second reaction zone 36 is operated under conditions to maintain a portion of the benzene feed in the vapor phase and to convert more of the benzene feed to a second mixed phase product in which most of cyclohexylbenzene is in the liquid phase and part of the benzene is in the vapor phase.

The second liquid phase product flows out of the second reaction zone 36 and is mixed with a third heated hydrogen stream in line 41 before flowing into the third reaction zone 37. Again the temperature of the third heated hydrogen stream can be adjusted to effect cooling of the second liquid phase product. In addition, the third reaction zone 37 is operated under conditions to maintain part of the benzene feed in the vapor phase and to convert more of the benzene feed to a third mixed phase product in which most of cyclohexylbenzene is in the liquid phase and part of the benzene is in the vapor phase. The third liquid phase product exits the reactor through line 42 for recovery of the desired cyclohexylbenzene.

The first, second and third vapor phase products exit their respective reaction zones 35, 36, and 37 through lines 43, 44, and 45 respectively and are combined and fed by line 46 to a heat exchanger 47. The combined vapor phase stream is cooled by the heat exchanger 47 so that benzene condenses from the stream. The cooled vapor stream is then passed to a flash drum 48 which separates the cooled vapor stream into a benzene-rich condensate stream and a further vapor stream. The benzene-rich condensate stream is removed from the flash drum 48 in line 49 and recycled to the line 31 for mixing with the fresh benzene feed. The further vapor stream, which is composed mainly of hydrogen, is removed from the flash drum 48 in line 51 and can be recycled to any or all of the reaction zones 35, 36, and 37.

Example 4

The invention according to FIG. 3 was simulated with a hydrogen to benzene feed molar ratio of 1:1. The results are provided in Table 4.

A summary of the results from Examples 1-4 is provided in Table 5. As shown, for comparable conversions and temperature rises in the reactor, the invention allows (a) a decrease in the hydrogen to benzene ratio; (b) a decrease in the cyclohexylbenzene recycled to the reactor; and (c) a decrease in the dicyclohexylbenzene production from the process.

Figure 4:
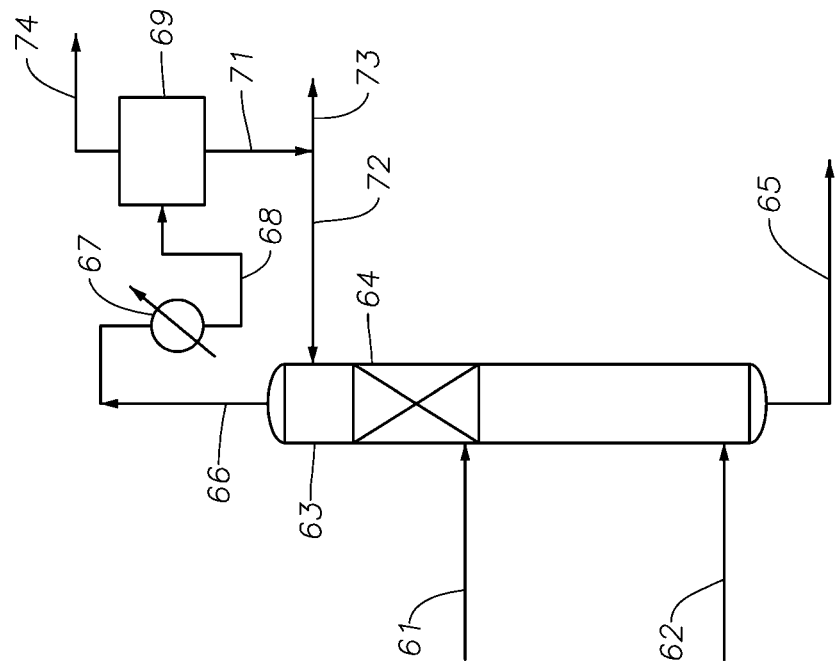
FIG. 4 is a schematic diagram of a process for producing cyclohexylbenzene according to a third example of the invention.

Referring now to FIG. 4, another inventive example is provided in which the benzene hydroalkylation is conducted in a catalytic distillation unit. In this example, benzene and hydrogen are fed by lines 61 and 62 respectively to a catalytic distillation tower 63 housing a catalyst bed 64 adjacent the top of the tower. The hydrogen is introduced adjacent the base of the tower 63 and the benzene is introduced into the portion of the tower 63 housing the catalyst bed 64. The benzene reacts with the hydrogen in the catalyst bed 64 and the conditions in the tower are such that the cyclohexylbenzene product flows in a liquid phase product stream out of the bed and down the tower, preventing further reaction to undesired products. The liquid phase product stream exits the tower through line 65.

The overhead stream from the tower 63 is composed mainly of hydrogen, benzene and cyclohexane and exits the top of the tower through line 66 and is directed to a heat exchanger 67. The overhead stream is cooled by the heat exchanger 67 and is then fed by line 68 to a flash drum 69 which separates the cooled overhead stream into a benzene-rich condensate stream and a further vapor stream. The benzene-rich condensate stream is removed from the flash drum 69 in line 71 and split into stream 72 which is recycled to the top of the tower 63 and stream 73 which is removed from the process to maintain by-product concentrations within desired limits (e.g., cyclohexane). The further vapor stream, which is composed mainly of hydrogen, is removed from the flash drum 69 in line 74 and can be recycled to the base of the tower 63.

Figure 5:
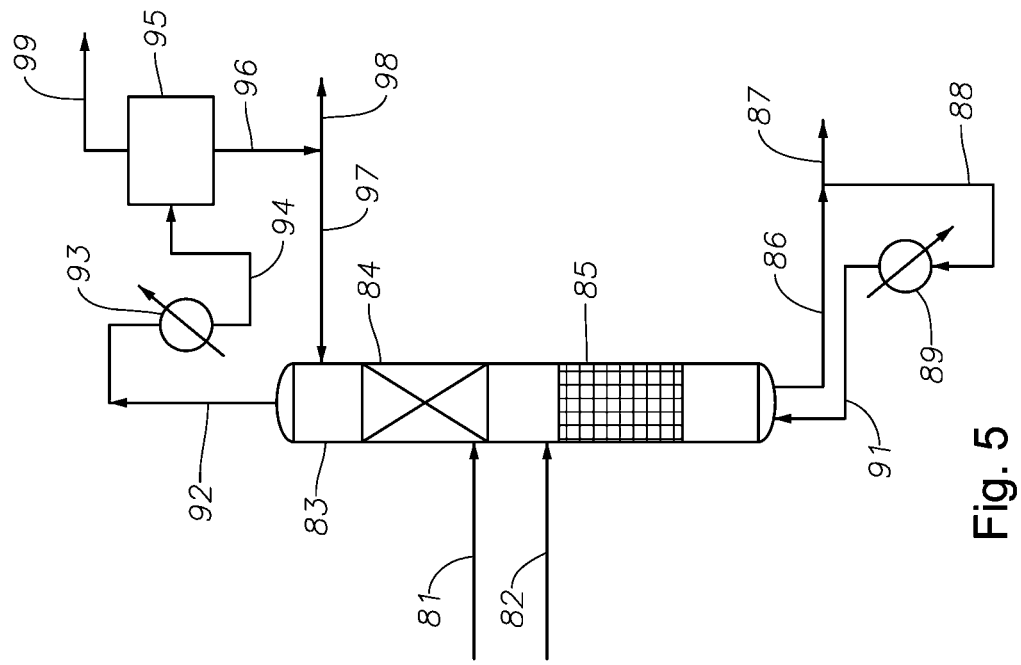
FIG. 5 is a schematic diagram of a process for producing cyclohexylbenzene according to a fourth example of the invention.

FIG. 5 illustrates a fourth example which is similar to the example of FIG. 4 but includes an additional separation zone and a reboiler to assist in recovery of any benzene entrained in the cyclohexylbenzene product stream. In the fourth example, benzene is introduced via line 81 to an upper portion of catalytic distillation tower 83 housing a catalyst bed 84, while hydrogen is introduced via line 82 to a central portion of the tower 83 between the catalyst bed 84 and a separation zone 85 located adjacent the base of the tower 83. As before, the benzene reacts with the hydrogen in the catalyst bed 84 and the conditions in the tower are such that the cyclohexylbenzene product flows in a liquid phase product stream out of the bed and down the tower, preventing further reaction to undesired products. The liquid phase product stream exits the tower 83 through line 86 and is split into two separate streams 87 and 88. Stream 87 is withdrawn from the process for recovery of the cyclohexylbenzene product, while stream 88 is vaporized by heat exchanger 89 and returned to the tower 83 as vapor stream 91. The vapor stream 91 passes up through the separation zone 85 and as in so doing vaporizes benzene entrained in the liquid cyclohexylbenzene product stream flowing down through the separation zone. The vaporized benzene then flows back into the catalyst bed 84 so as to be available for the hydroalkylation reaction.

As in the case of the third example, the overhead tower 83 (composed mainly of hydrogen, benzene, and cyclohexane) exits the top of the tower through line 92 and is directed to a heat exchanger 93. The overhead is cooled by the heat exchanger 93 and is then fed by line 94 to a flash drum 95, which separates the cooled overhead into a benzene-rich condensate stream and a further vapor stream. The benzene-rich condensate stream is removed from the flash drum 95 in line and split into stream 97 which is recycled to the top of the tower 83 and stream 98 which is removed from the process. The further vapor stream, which is composed mainly of hydrogen, is removed from the flash drum 95 in line 99 and can be recycled to the tower 83 with the fresh hydrogen in line 82.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

TABLE 1

| Stream # | 1 | 2 | 4 | 6 | 8 | 9 | 10 | 27 | 28 |
|---|---|---|---|---|---|---|---|---|---|
| | | | | Conventional | | | | | |
| Phase | Vapor | Liquid | Mixed | Mixed | Liquid | Vapor | Liquid | Liquid | Liquid |
| Temp. (° C.) | 145.00 | 145.00 | 145.00 | 154.77 | 154.77 | 154.77 | 154.77 | 154.77 | 50.00 |
| Pressure (bar) | 12.39 | 12.39 | 12.39 | 12.39 | 12.39 | 12.39 | 12.39 | 12.39 | 12.39 |
| Total Mass Rate (kg/hr) | 201.59 | 11717.04 | 33065.55 | 33065.50 | 25869.90 | 7195.61 | 21146.26 | 4723.65 | 21146.26 |
| | | | | Mass Flow Rates (kg/hr) | | | | | |
| Hydrogen | 201.59 | 0.00 | 203.96 | 180.09 | 2.91 | 177.18 | 2.37 | 0.53 | 2.37 |
| Benzene | 0.00 | 11717.04 | 29515.82 | 28723.10 | 21775.33 | 6947.79 | 17799.32 | 3976.01 | 17799.32 |
| Methylcyclopentane | 0.00 | 0.00 | 0.52 | 0.91 | 0.64 | 0.27 | 0.52 | 0.12 | 0.52 |
| Cyclohexane | 0.00 | 0.00 | 94.32 | 156.71 | 115.39 | 41.32 | 94.32 | 21.07 | 94.32 |
| Cyclohexylbenzene | 0.00 | 0.00 | 2980.99 | 3674.24 | 3645.84 | 28.41 | 2980.14 | 665.70 | 2980.14 |
| Bicyclohexane | 0.00 | 0.00 | 2.43 | 2.99 | 2.96 | 0.03 | 2.42 | 0.54 | 2.42 |
| Dicyclohexylbenzene | 0.00 | 0.00 | 170.54 | 208.39 | 208.33 | 0.06 | 170.29 | 38.04 | 170.29 |

TABLE 2

| Stream # | 11 | 12 | 15 | 18 | 21 | 22 | 11 | 26 | 25 |
|---|---|---|---|---|---|---|---|---|---|
| Phase | Vapor | Liquid | Mixed | Mixed | Liquid | Vapor | Mixed | Liquid | Vapor |
| Temp. (° C.) | 145.00 | 145.00 | 145.00 | 154.22 | 154.22 | 154.22 | 50.00 | 50.00 | 50.00 |
| Pressure (bar) | 12.39 | 12.39 | 12.39 | 12.39 | 12.39 | 12.39 | 12.39 | 12.39 | 12.39 |
| Total Mass Rate (kg/hr) | 302.39 | 11717.04 | 23701.16 | 23701.16 | 11413.93 | 12287.24 | 12287.24 | 11681.72 | 605.52 |
| | | | | Mass Flow Rates (kg/hr) | | | | | |
| Hydrogen | 302.39 | 0.00 | 303.79 | 279.01 | 1.25 | 277.76 | 277.76 | 1.35 | 276.41 |
| Benzene | 0.00 | 11717.04 | 23302.26 | 22465.39 | 10554.47 | 11910.93 | 11910.93 | 11585.06 | 325.87 |
| Methylcyclopentane | 0.00 | 0.00 | 0.49 | 0.86 | 0.34 | 0.52 | 0.52 | 0.49 | 0.03 |

TABLE 2-continued

| Stream # | 11 | 12 | 15 | 18 | 21 | 22 | 11 | 26 | 25 |
|---|---|---|---|---|---|---|---|---|---|
| Cyclohexane | 0.00 | 0.00 | 72.79 | 135.57 | 59.44 | 76.13 | 76.13 | 72.92 | 3.21 |
| Cyclohexylbenzene | 0.00 | 0.00 | 21.51 | 794.59 | 773.08 | 21.51 | 21.51 | 21.51 | 0.00 |
| Bicyclohexane | 0.00 | 0.00 | 0.00 | 0.12 | 0.12 | 0.00 | 0.00 | 0.00 | 0.00 |
| Dicyclohexylbenzene | 0.00 | 0.00 | 0.01 | 9.51 | 9.50 | 0.01 | 0.01 | 0.01 | 0.00 |

TABLE 3

| Stream # | 11 | 12 | 15 | 18 | 21 | 22 | 11 | 26 | 25 |
|---|---|---|---|---|---|---|---|---|---|
| Phase | Vapor | Liquid | Mixed | Mixed | Liquid | Vapor | Mixed | Liquid | Vapor |
| Temp. (° C.) | 145.00 | 145.00 | 145.00 | 156.89 | 156.89 | 156.89 | 50.00 | 50.00 | 50.00 |
| Pressure (bar) | 12.39 | 12.39 | 12.39 | 12.39 | 12.39 | 12.39 | 12.39 | 12.39 | 12.39 |
| Total Mass Rate (kg/hr) | 201.59 | 11717.04 | 20237.08 | 20237.08 | 11534.23 | 8702.86 | 8702.86 | 8318.44 | 384.41 |
| Mass Flow Rates (kg/hr) | | | | | | | | | |
| Hydrogen | 201.59 | 0.00 | 202.55 | 177.67 | 1.21 | 176.46 | 176.46 | 0.96 | 175.50 |
| Benzene | 0.00 | 11717.04 | 19968.56 | 19118.27 | 10659.76 | 8458.52 | 8458.52 | 8251.54 | 206.97 |
| Methylcyclopentane | 0.00 | 0.00 | 0.35 | 0.71 | 0.34 | 0.36 | 0.36 | 0.35 | 0.02 |
| Cyclohexane | 0.00 | 0.00 | 49.04 | 107.79 | 56.86 | 50.93 | 50.93 | 49.01 | 1.92 |
| Cyclohexylbenzene | 0.00 | 0.00 | 16.29 | 806.25 | 789.97 | 16.29 | 16.29 | 16.29 | 0.00 |
| Bicyclohexane | 0.00 | 0.00 | 0.00 | 0.12 | 0.12 | 0.00 | 0.00 | 0.00 | 0.00 |
| Dicyclohexylbenzene | 0.00 | 0.00 | 0.01 | 9.69 | 9.68 | 0.01 | 0.01 | 0.01 | 0.00 |

TABLE 4

| Stream # | 31 | 33 | 34 | 36 | 43 | 39 | 44 |
|---|---|---|---|---|---|---|---|
| Phase | Liquid | Liquid | Vapor | Mixed | Vapor | Vapor | Vapor |
| Temp. (° C.) | 145.00 | 127.59 | 145.00 | 135.21 | 145.27 | 145.00 | 145.36 |
| Pressure (bar) | 12.39 | 12.39 | 12.39 | 12.39 | 12.39 | 12.39 | 12.39 |
| Total Mass Rate (kg/hr) | 11717.04 | 14586.38 | 39.91 | 14626.30 | 999.91 | 39.91 | 1032.66 |
| Mass Flow Rates (kg/hr) | | | | | | | |
| Hydrogen | 0.00 | 0.33 | 39.91 | 40.25 | 30.12 | 39.91 | 31.61 |
| Benzene | 11717.04 | 14562.44 | 0.00 | 14562.44 | 965.15 | 0.00 | 992.88 |
| Methylcyclopentane | 0.00 | 0.10 | 0.00 | 0.10 | 0.02 | 0.00 | 0.04 |
| Cyclohexane | 0.00 | 21.00 | 0.00 | 21.00 | 4.25 | 0.00 | 7.33 |
| Cyclohexylbenzene | 0.00 | 2.46 | 0.00 | 2.46 | 0.36 | 0.00 | 0.80 |
| Bicyclohexane | 0.00 | 0.00 | 0.00 | 0.00 | 0.00 | 0.00 | 0.00 |
| Dicyclohexylbenzene | 0.00 | 0.00 | 0.00 | 0.00 | 0.00 | 0.00 | 0.00 |

| Stream # | 41 | 42 | 45 | 46 | 52 | 49 | 51 |
|---|---|---|---|---|---|---|---|
| Phase | Vapor | Liquid | Vapor | Vapor | Mixed | Liquid | Vapor |
| Temp. (° C.) | 145.00 | 145.12 | 145.12 | 145.25 | 50.00 | 50.00 | 50.00 |
| Pressure (bar) | 12.39 | 12.39 | 12.39 | 12.39 | 12.39 | 12.39 | 12.39 |
| Total Mass Rate (kg/hr) | 41.12 | 11631.14 | 1043.62 | 3076.19 | 3076.19 | 2869.35 | 206.84 |
| Mass Flow Rates (kg/hr) | | | | | | | |
| Hydrogen | 41.12 | 1.40 | 32.95 | 94.67 | 94.67 | 0.33 | 94.34 |
| Benzene | 0.00 | 10824.44 | 998.60 | 2956.64 | 2956.64 | 2845.46 | 111.21 |
| Methylcyclopentane | 0.00 | 0.41 | 0.05 | 0.11 | 0.11 | 0.10 | 0.01 |
| Cyclohexane | 0.00 | 100.13 | 10.69 | 22.27 | 22.27 | 20.99 | 1.28 |
| Cyclohexylbenzene | 0.00 | 686.58 | 1.30 | 2.46 | 2.46 | 2.46 | 0.00 |
| Bicyclohexane | 0.00 | 0.15 | 0.00 | 0.00 | 0.00 | 0.00 | 0.00 |
| Dicyclohexylbenzene | 0.00 | 8.26 | 0.00 | 0.00 | 0.00 | 0.00 | 0.00 |

TABLE 5

| Parameter | Example 1 | Example 2 | Example 3 | Example 4 |
|---|---|---|---|---|
| Benzene Flow rate entering process (kg/hr) | 150 | 150 | 150 | 150 |
| Hydrogen to benzene ratio entering reactor | 1:1.5 | 1:1 | 1:1.5 | 0.4:1 |
| Benzene Conversion (%) | 6.8 | 7.1 | 7.3 | 6.7 |
| Temperature rise in reactor bed (° C.) | 9.8 | 9.2 | 11.9 | 10.1 (Bed 1), 10.4 (Bed 2) and 10.8 (Bed 3) |
| Amount of cyclohexylbenzene recycled (kg mol/hr) | 18.6 | 0.134 | 0.101 | 0.015 |

TABLE 5-continued

| Parameter | Example 1 | Example 2 | Example 3 | Example 4 |
|---|---|---|---|---|
| Amount of dicyclohexylbenzene in product from process (kg mol/hr) | 0.157 | 0.039 | 0.04 | 0.034 |

The invention claimed is:

1. A process for producing cyclohexylbenzene comprising:
   (a) contacting hydrogen and benzene in a first reaction zone under conditions effective to produce a product effluent comprising cyclohexylbenzene and residual benzene, wherein at least a portion of the residual benzene is in the vapor phase and at least a portion of the cyclohexylbenzene is in the liquid phase;
   (b) separating the product effluent into (i) a first stream that is rich in residual benzene in the vapor phase as compared to the product effluent; and (ii) a second stream that is rich in cyclohexylbenzene in the liquid phase as compared to the product effluent;
   (c) cooling at least a portion of the first stream to condense at least a portion of the residual benzene in the vapor phase to the liquid phase and produce a condensate stream; and
   (d) recycling at least a portion of the condensate stream to the first reaction zone.

2. The process of claim 1, wherein at least 5 wt % of the residual benzene in the product effluent is in the vapor phase, the wt % based upon the weight of the product effluent.

3. The process of claim 1, wherein at least 25 wt % of the residual benzene in the product effluent is in the vapor phase, the wt % based upon the weight of the product effluent.

4. The process of claim 1, wherein at least 50 wt % of the first stream is residual benzene in the vapor phase, the wt % based upon the weight of the first stream.

5. The process of claim 1, wherein the first stream further comprises cyclohexane and, after removal of the condensate stream in the cooling step (c), at least a portion of the remaining first stream is contacted with a dehydrogenation catalyst under dehydrogenation conditions effective to convert cyclohexane to benzene.

6. The process of claim 5, wherein the dehydrogenation conditions comprise a temperature between 330° C. and 550° C. and a pressure between 100 kPa and 1000 kPa.

7. The process of claim 1, wherein the condensate stream contains less than 0.5 wt % of cyclohexylbenzene, based upon the total weight of the condensate stream.

8. The process of claim 1, wherein (c) comprises cooling the first stream by at least 10° C.

9. The process of claim 1, wherein (c) comprises cooling the first stream to a temperature of 150° C. or less.

10. The process of claim 1, wherein the contacting (a) is conducted in the presence of a stoichiometric excess of hydrogen.

11. The process of claim 1, wherein the product effluent further comprises dicyclohexylbenzene, and the second stream is rich in dicyclohexylbenzene as compared to the product effluent.

12. The process of claim 1, wherein the hydrogen is fed to the first reaction zone in a plurality of locations.

13. The process of claim 1, wherein the first reaction zone contains a catalyst comprising at least one molecular sieve and at least one hydrogenation metal.

14. The process of claim 13, wherein the at least one molecular sieve is selected from zeolite beta, mordenite, zeolite X, zeolite Y, and a molecular sieve of the MCM-22 family.

15. The process of claim 13, wherein said at least one hydrogenation metal is selected from palladium, ruthenium, nickel, zinc, tin, and cobalt.

16. The process of claim 1, wherein the second stream further comprises residual benzene from (a), and at least a portion of the second stream is fed to a second reaction zone where the residual benzene is contacted with hydrogen under hydroalkylation conditions to produce a further product effluent comprising cyclohexylbenzene and further residual benzene, wherein at least a portion of the further residual benzene in the further product effluent is in the vapor phase.

17. The process of claim 16, wherein the process further comprises:
   (e) separating the further product effluent into a third stream that is rich in the further residual benzene in the vapor phase as compared to the further product effluent, and a fourth stream that is rich in the cyclohexylbenzene in the liquid phase as compared to the further product effluent;
   (f) cooling at least a portion of the third stream to condense at least a portion of the further residual benzene in the vapor phase to the liquid phase and produce a second condensate stream; and
   (g) recycling at least a portion of the second condensate stream to at least one of the first reaction zone and the second reaction zone.

18. The process of claim 16, wherein hydrogen is separately supplied to the first reaction zone and the second reaction zone.

19. The process of claim 17, wherein at least one of the separating steps (b) and (e) is conducted in a flash vessel or using catalytic distillation.

20. The process of claim 17, wherein at least a portion of the second stream and/or the fourth stream is vaporized and recycled to at least one of the first reaction zone and the second reaction zone.

21. A process for producing cyclohexylbenzene comprising:
   (a) contacting hydrogen and benzene in a first reaction zone under conditions effective to produce a first product effluent comprising cyclohexylbenzene and residual benzene, wherein at least a portion of the residual benzene is in the vapor phase;
   (b) separating the first product effluent into (i) a first stream that is rich in residual benzene in the vapor phase as compared to the first product effluent; and (ii) a second stream that comprises residual benzene and is rich in cyclohexylbenzene in the liquid phase as compared to the first product effluent;
   (c) contacting the second stream with hydrogen in a second reaction zone under conditions effective to convert at least a portion of the residual benzene to cyclohexylbenzene and produce a second product effluent comprising cyclohexylbenzene and further residual benzene, wherein at least a portion of the further residual benzene is in the vapor phase;
   (d) separating the second product effluent into a third stream that is rich in further residual benzene in the vapor phase as compared to the second product effluent, and a fourth stream that is rich in cyclohexylbenzene in the liquid phase as compared to the second product effluent;

(e) cooling at least a portion of the first stream and the third stream to condense at least a portion of the residual benzene and further residual benzene and produce a condensate stream; and
(f) recycling at least a portion of the condensate stream to at least one of the first reaction zone and the second reaction zone.

22. A process for producing phenol comprising:
(a) contacting benzene and hydrogen in a first reaction zone under conditions effective to produce a product effluent comprising cyclohexylbenzene and residual benzene, wherein at least a portion of the residual benzene is in the vapor phase;
(b) separating the product effluent into (i) a first stream that is rich in residual benzene in the vapor phase as compared to the product effluent; and (ii) a second stream that is rich in cyclohexylbenzene in the liquid phase as compared to the product effluent;
(c) cooling at least a portion of the first stream to condense at least a portion of the residual benzene and produce a condensate stream that is rich in residual benzene;
(d) recycling at least a portion of the condensate stream to the first reaction zone;
(e) oxidizing at least a portion of the second stream under conditions sufficient to form at least some cyclohexylbenzene hydroperoxide; and
(f) cleaving at least a portion of the cyclohexylbenzene hydroperoxide to form phenol and cyclohexanone.

* * * * *